United States Patent [19]

Ireland et al.

[11] 4,044,063

[45] Aug. 23, 1977

[54] METHOD FOR ALTERING THE PRODUCT DISTRIBUTION OF WATER WASHED, FISCHER-TROPSCH SYNTHESIS HYDROCARBON PRODUCT TO IMPROVE GASOLINE OCTANE AND DIESEL FUEL YIELD

[75] Inventors: Henry R. Ireland, Woodbury; Thomas R. Stein, Cherry Hill, both of N.J.

[73] Assignee: Mobil Oil Corporation, New York, N.Y.

[21] Appl. No.: 614,589

[22] Filed: Sept. 18, 1975

[51] Int. Cl.[2] .................... C07C 1/04

[52] U.S. Cl. .................... 260/676 R; 208/79; 208/88; 208/93; 208/120; 208/135; 260/449 R; 260/450

[58] Field of Search .............. 260/676, 449 R, 449 M, 260/449.5, 449.6, 450; 208/57, 64, 79, 88, 93

[56] References Cited

U.S. PATENT DOCUMENTS

| | | | |
|---|---|---|---|
| 2,740,804 | 4/1956 | Glazier | 260/450 |
| 2,752,382 | 6/1956 | Garrett et al. | 260/450 |
| 3,172,842 | 3/1965 | Peterson | 208/79 |
| 3,700,585 | 10/1972 | Chen et al. | 208/111 |
| 3,729,409 | 4/1973 | Chen | 208/135 |
| 3,760,024 | 9/1973 | Cattanach | 260/673 |
| 3,843,510 | 10/1974 | Morrison et al. | 208/111 |
| 3,928,483 | 12/1975 | Chang et al. | 260/668 R |
| 3,960,978 | 6/1976 | Givens et al. | 260/683.15 R |

OTHER PUBLICATIONS

Asinger, Paraffins Chemistry & Technology, Pergammon Press, N.Y. (1968), pp. 3, 123-125, 131, 132, 136, 138.

*Primary Examiner*—C. Davis
*Attorney, Agent, or Firm*—Charles A. Huggett; Carl D. Farnsworth

[57] ABSTRACT

Upgrading of Fischer-Tropsch synthesis product is accomplished by water washing the product effluent to separate oxygenates therefrom, separating the washed effluent to recover a $C_3$-$C_4$ rich fraction, a $C_5$ plus gasoline fraction, a light fuel oil fraction and a heavy fuel oil fraction which is subjected to hydrodewaxing conditions to produce additional light fuel oil and gasoline boiling product. The light fuel oil products were hydrotreated and the synthesis gasoline is octane improved with ZSM5 crystalline zeolite.

7 Claims, 1 Drawing Figure

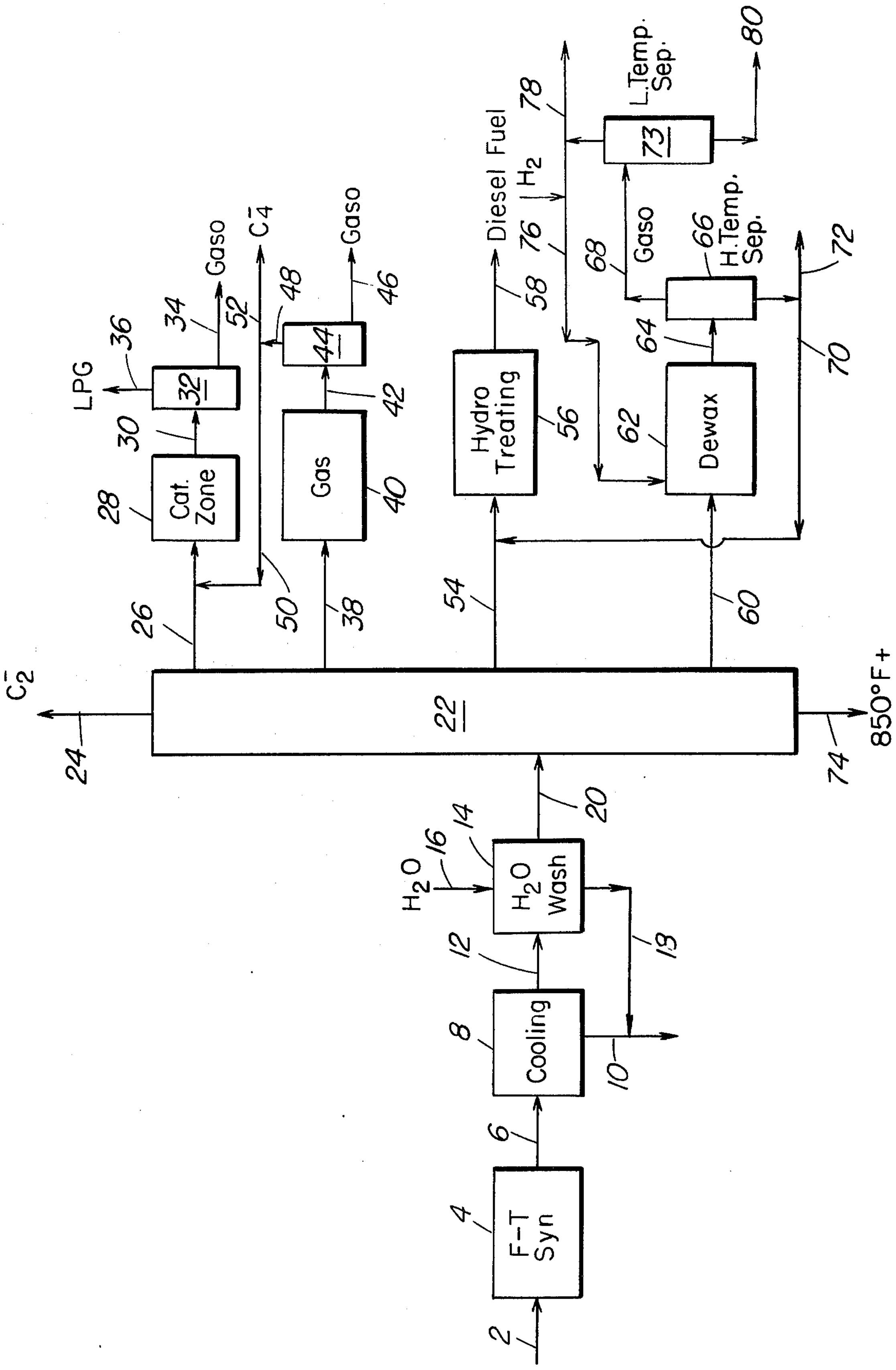
F–T Syn
Cooling
$H_2O$ Wash
$H_2O$
22
$C_2^-$
850°F+
Cat. Zone
32
LPG
Gaso
$C_4^-$
Gas
44
Gaso
Hydro Treating
Diesel Fuel
$H_2$
Dewax
H.Temp. Sep.
Gaso
73
L.Temp. Sep.
2
4
6
8
10
12
13
14
16
20
24
26
28
30
34
36
38
40
42
46
48
50
52
54
56
58
60
62
64
66
68
70
72
74
76
78
80

METHOD FOR ALTERING THE PRODUCT DISTRIBUTION OF WATER WASHED, FISCHER-TROPSCH SYNTHESIS HYDROCARBON PRODUCT TO IMPROVE GASOLINE OCTANE AND DIESEL FUEL YIELD

BACKGROUND OF THE INVENTION

This invention is concerned with a method or process for converting synthesis gas, such as mixtures of gaseous carbon oxides with hydrogen or hydrogen donors to form hydrocarbon mixtures and oxygenates. The invention is concerned with an arrangement of processing steps for increasing the yields of high octane gasoline boiling components and light oil materials suitable for use as diesel fuel over that obtained heretofore in the known Fischer-Tropsch synthesis gas conversion process. In still another aspect, this invention is concerned with the use of a novel class of crystalline zeolites represented by ZSM-5 crystalline zeolite for improving the product distribution obtained from a Fischer-Tropsch synthesis gas conversion operation.

The world's largest oil from coal producing plant is known as the Sasol project in South Africa where petroleum products and chemicals are producted from high ash bituminous coal. The Sasol project works two variations of the Fischer-Tropsch synthesis gas conversion operation using a fixed and fluid catalyst bed system. This Sasol project has been described in British Chemical Engineering for the months May, June and July 1957. One portion of these articles of particular interest is concerned with the product recovery that is discussed in the July 1957 article.

The Sasol project referred to above and built to convert an abundant supply of coal to hydrocarbons, oxygenates and chemicals was a pioneering venture. The process complex developed is enormous by any standard and quite expensive to operate. Therefore any advances which can be made to improve the yield of desired products without significantly increasing operating expense is viewed as one of major importance. The processing concepts of this invention are considered to fall in that category.

OTHER PRIOR ART

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, or of hydrogen and carbon monoxide and carbon dioxide, are well known. Although various processes may be employed for the gasification, those of major importance depend either on the partial combustion of the fuel with an oxygen-containing gas or on a combination of these two reactions. An exellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publishers, New York, N.Y., the contents of which are herein incorporated by reference. The techniques for gasification of coal or other solid, liquid or gaseous fuel are not considered to be per se inventive here.

It is considered desirable to effectively and more efficiently convert synthesis gas, and thereby coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, at from about 300° F to about 850° F under from about one to one thousand atmospheres pressure, over a fairly wide variety of catalysts. The Fischer-Tropsch process, for example, which has been most extensively studied, produces a range of products including liquid hydrocarbons, a portion of which have been used as low octane gasoline. The types of catalysts that have been studied for this and related processes include those based on metals or oxides of iron, cobalt, nickel, ruthenium, thorium, rodium and osmium.

The wide range of catalysts and catalysts modifications disclosed in the art and an equally wide range of conversion conditions for the reduction of carbon monoxide by hydrogen provide considerable flexibility toward obtaining selected boiling-range products. Nonetheless, in spite of this flexibility, it has not proved possible to make such selections so as to produce liquid hydrocarbons in the gasoline boiling range which contain highly branched paraffins and substantial quantities of aromatic hydrocarbons, both of which are required for high quality gasoline, or to selectively produce aromatic hydrocarbons particularly rich in the benzene to xylenes range. A review of the status of this art is given in "Carbon Monoxide-Hydrogen Reactions", Encyclopedia of Chemical Technology, Edited by Kirk-Othmer, Second Edition, Volume 4, pp. 446–488, Interscience Publishers, New York, N.Y., the text of which is incorporated herein by reference.

SUMMARY OF THE INVENTION

This invention is concerned with improving the product distribution of a Fischer-Tropsch synthesis gas conversion operation. In a particular aspect the present invention is concerned with improving the yield of diesel fuels and the octane rating of gasoline product obtained in the combination operation.

In the combination operation of this invention we begin with the product effluent of a Fischer-Tropsch synthesis gas operation such as might be obtained by the Sasol project above identified. The Fischer-Tropsch synthesis gas operation is known to produce a wide spectrum of products including fuel gas, light olefins, LPG, gasoline, light and heavy fuel oils, waxy oils and oxygenates indentified as alcohols, acetone, ketones, and acids. The acids are identified as acetic and propionic acid.

In the combination operation of this invention it is desirable to recover the oxygenates for conversion to desirable chemicals and to maximize the recovery of diesel fuels. Broadly speaking this is accomplished by water washing the total effluent of the Fischer-Tropsch synthesis operation to maximize the recovery of oxygenates and thereafter separating the washed hydrocarbon effluent into particular segments for processing as herein provided. Recovery and conversion of the oxygenates in the water wash is not a part of the processing combination of this invention.

In the combination operation of this invention, distillation of the washed Fischer-Tropsch synthesis hydrocarbon effluent is accomplished under conditions identified with altering distillation cutpoints, recovering at least two separate distillate fractions thereafter processed to maximize diesel fuel product, hydrodewaxing a heavy distillate fraction under selected conditions and hydrotreating diesel fuel products of the process under conditions improving storage stability when required. Improving the octane rating of gasoline product of the process is also an important step of the combination operation.

The improvements attributed to the combination operation of this invention are not all associated with processing inventions but in large part are contributions by a novel class of crystalline zeolites and the processing conditions in which employed.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

Thus, it should be understood that the "Constraint Index" value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application, Ser. No. 358,192, filed May 7, 1973, and now abandoned the entire contents of which are incorporated herein by reference, describes a zeolite composition, and a method of making such, designated as ZSM-21 which is useful in this invention.

U.S. application Ser. No. 528,061 filed Nov. 29, 1974, the entire contents of which are incorporated herein by reference, describes a zeolite composition including a method of making it. This composition is designated ZSM-35 and is useful in this invention.

U.S. application Ser. No. 528,060, filed Nov. 29, 1974, and now abandoned the entire contents of which are incorporated herein by reference, describes a zeolite composition including a method of making it. This composition is designated ZSM-38 and is useful in this invention.

The X-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, and ZSM-21, with ZSM-5 particularly preferred.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| GAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below abcut 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |

-continued

| Zeolite | Void Volume | Framework Density |
|---|---|---|
| Gmelinite | .44 | 1.46 |
| Chabazite | .47 | 1.45 |
| A | .5 | 1.3 |
| Y | .48 | 1.27 |

The drawing is a block flow diagrammatic sketch in elevations of one arrangement for separating the product effluent of Fischer-Tropsch synthesis and upgrading products thus separated to improve the yield of diesel products and gasoline yield of improved octane rating.

Referring now to the drawing, a synthesis gas comprising oxides of carbon and hydrogen are introduced by conduit 2 to a Fischer-Tropsch synthesis gas conversion operation represented by zone 4. In zone 4, the synthesis gas is converted to hydrocarbons and oxygenates in a manner known in the prior art herein before identified. The product effluent thus obtained is passed by conduit 6 to a cooling section 8 wherein cooling and separation of a water product phase containing oxygenates is obtained. The water phase is withdrawn by conduit 10. A hydrocarbon phase and gaseous products of the Fischer-Tropsch synthesis operation is withdrawn by conduit 12 and passed to a water wash step represented by zone 14. Wash water is introduced to zone 14 by conduit 16 wherein additional oxygenates are removed from the hydrocarbon phase passed thereto. The wash water with oxygenates is removed from zone 14 by conduit 18 and combined with the water phase in conduit 10 for further processing recovery known in the art.

The washed hydrocarbon phase is then passed by conduit 20 to a fractionation section such as an atmospheric fractionation zone 22. Furnace means not shown are provided in conduit 20 for heating to a temperature of about 700°-800° F the water washed effluent charged to zone 22.

In fractionation section 22, temperature and pressure conditions are maintained suitable to provide the product segments hereinafter discussed. In one specific embodiment a $C_2$ gaseous material and comprising unreacted carbon oxides and hydrogen is withdrawn as by conduit 24. This gaseous material may be used as fuel gas or a portion thereof may be recycled directed to the Fischer-Tropsch synthesis reactor or after suitable reforming thereof then passed to the Fischer-Tropsch synthesis zone.

A $C_3$-$C_5$ product material is withdrawn by conduit 26 and passed to zone 28 which may be used for catalytic polymerization zone or alkylation zone. On the other hand, it is contemplated employing a ZSM-5 crystalline zeolite catalyst in zone 28 in place of the others referred to above for catalytic operations effecting the formation of LPG products and/or gasoline boiling materials. The products of zone 28 are passed by conduit 30 to a separation zone 32 wherein gasoline boiling material is separated and withdrawn by conduit 34. Lower boiling gaseous materials such as LPG gases are withdrawn by conduit 36.

A gasoline boiling range product fraction is recovered from distillation section 22 by conduit 38 which is then passed to zone 40. This gasoline fraction will normally comprise materials boiling in the range of $C_5$ to 320° F. Under some circumstances it may be desirable to increase the end point of this material up to 330 or even 360° F or 380° F. In zone 40, the gasoline boiling fraction of an octane rating of about 55 is brought in contact with a special class of crystalline zeolite catalysts represented by ZSM-5 crystalline zeolite maintained at a temperature within the range of 500° F to 800° F, at a pressure within the range of 0 to 100 psig. In this operation the synthesis gasoline product is improved in octane rating up to at least 90. The product of this gasoline upgrading is passed by conduit 42 to separation zone 44 wherein a separation is made to recover $C_5$ plus gasoline boiling material withdrawn by conduit 46 from lower boiling $C_4$ minus material withdrawn by conduit 48. This $C_4$ minus product fraction may be recycled by conduit 50 to conduit 26 communicating with zone 28. On the other hand, all or a portion of this $C_4$ minus material may be withdrawn by conduit 52.

As mentioned above, one purpose of the combination operation of this invention is to improve the yield of diesel fuel products. In accomplishing this objective, a light fuel oil product boiling in the range of from about 320° F up to about 600° F is withdrawn from separation section 22 by conduit 54 and passed to a hydrotreating zone 56. In hydrotreating zone 56, this light fuel oil product is contacted with hydrogen under hydrogenating conditions of temperature within the range of 500° to 800° F and pressure within the range of 200 to 1000 psig. Catalysts suitable for hydrotreating the light fuel oil product include cobalt-molybdenum or nickel molybdenum on alumina and other known hydrogenation catalysts of the prior art.

The hydrotreated light fuel oil is recovered from zone 56 by conduit 58.

A heavy fuel oil product fraction boiling in the range of about 600° F up to about 850° F is recovered and withdrawn from separation section 22 by conduit 60 for passage to hydrodewaxing zone 62. In hydrodewaxing zone 62, the heavy fuel oil is brought in contact with a ZSM-5 crystalline zeolite conversion catalyst and hydrogen (via conduit 76) under temperature conditions within the range of 500° to 800° F and a hydrogen pressure within the range of 100 to 1500 psi. More usually the hydrogen pressure will be about 400 psi using a hydrogen recycle rate of about 2500 SCF/B. In this hydrodewaxing operation conversion of the 600 to 850° F boiling fraction is such as to produce gasoline boiling material and heavy fuel oil material suitable for blending with the light oil fraction before or after hydrogenation. The product of dewaxing in zone 62 is passed by conduit 64 to a high temperature separation zone 66 wherein a separation is made to recover gasoline and lighter boiling material withdrawn by conduit 68 from higher boiling material withdrawn by conduit 70. The gasoline and lighter material in conduit 68 is passed to a second separate low temperature separation zone 73 after further cooling thereof sufficient to produce a hydrogen rich gaseous product stream withdrawn by conduit 76. This hydrogen rich steam is compressed in a compressor not shown and recycled by conduit 76 to the hydrode-waxing zone 62. Excess $C_2$ minus hydrogen rich gas not recycled is withdrawn by conduit 78 for use as desired — such as recycle gas to the Fischer-Tropsch unit or a synthesis gas producing unit. An unstabilized gasoline product is withdrawn from zone 73 by conduit 80. This unstable gasoline product may be stabilized before blending with other gasoline products of the process. The heavy dewaxed fuel oil product of hydrodewaxing obtained as above provided is withdrawn by conduit 70 and and thereafter preferably passed to the hydrotreating zone 56 for further stabilization and color improvement when required. On the other hand, all or a portion of this heavy fuel oil product may be withdrawn by conduit 72 for further use as desired.

The table presented below particularly concerns itself with improving the yield of fuel oil product such as a diesel fuel oil product from the combination operation of this invention. The yield of hydrodewaxed fuel oil product meeting pour point specification requirements made from the 600° to 850° F heavy waxy products is about 80%. The gasoline product of this hydrodewaxing operation was 89 clear and 97 + 3 octane. It can be employed in the gasoline pool of the process. The table below identifies the method of forming and the yield of fuel oil product obtained when following the processing concepts of the present invention.

TABLE

| MAXIMIZING FUEL OIL PRODUCT FROM FISCHER-TROPSCH PRODUCT | | |
|---|---|---|
| Fischer-Tropsch Decant Oil | | |
| | Wt.% | Vol.% |
| Light Distillate | 33.0 | 35.0 |
| 600–850° F Heavy Distillate | 52.0 | 52.0 |
| 850+° F Bottoms | 15.0 | 13.0 |
| Operating Conditions | | |
| $H_2$ Pressure, psi | 400 | |
| LHSV, V/Hr/V | 1.5 | |
| $H_2$ Circulation, SCF/B | 2500 | |
| Temperature, ° F | 550–750 | |
| Hydrodewaxer Yields | Wt.% | Vol.% |
| (Chg: 600–850° F Hvy.Dist., 29.5° API) | | |
| $H_2O$ | 1.47 | — |
| $C_1$ | 0.03 | — |
| $C_2$ | 0.07 | — |
| $C_3$ | 0.72 | — |
| $C_4$ | 2.5 | 3.8 |
| $C_5$ | 3.0 | 4.1 |
| $C_6$ - 330° F Naphtha | 13.2 | 15.3 |
| 330+° F Distillate | 79.3 | 79.2 |
| | 100.32 | |
| Hydrogen Consumption, SCF/B | 190 | |
| Product Quality | | |
| $C_6$ - 330° F Naphtha | | |
| Gravity, ° API | 55.0 | |
| Paraffins | 28 | |
| Olefins | 35 | |
| Naphthenes | 13 | |
| Aromatics | 24 | |
| Octane R+O/R+3 | 89/97 | |
| HDW Distillate | | |
| Gravity, ° API | 29.2 | |
| Pour Point, ° F. | 20 | |
| Aniline Point | 128 | |
| Viscosity, KV at 100° F, cs | 6.01 | |

The Fischer-Tropsch Synthesis operation discussed produces under some conditions a relatively small amount of material boiling 850° F and higher. Generally this material is in such small quantity that processing is not warranted. Therefore such material is withdrawn from a bottom portion of fractionation section 22 by conduit 74. This material may be burned as fuel in the process or disposed of in some other suitable manner not considered in this process.

In the combination operation above discussed the yield of diesel fuel is increased by as much as about 120% and the Fischer-Tropsch synthesis gasoline product is improved by at least 20 octane numbers.

In the combination operation of this invention it is contemplated separating the oxygenates recovered from the effluent of the Fischer-Tropsch operation to recover all or a portion of the lower alcohols such as methanol and ethanol and convert these separated oxygenates to hydrocarbons as by contact with the special zeolite catalysts herein identified. On the other hand it is contemplated separating all of a portion of the oxygenates from the water phase and converting the oxygenates thus recovered to hydrocarbons by contact with the special zeolite catalysts herein identified.

Having thus generally described the improved processing combination of this invention and described a specific example in support thereof, it is to be understood that no undue restrictions are to be imposed by reason thereof except as defined by the following claims.

We claim:

1. A method for upgrading products of Fischer-Tropsch Synthesis comprising hydrocarbon and oxygenates which comprises, cooling the product of Fischer-Tropsch Synthesis sufficient to recover a water phase separately from a liquid hydrocarbon phase and a gaseous phase comprising hydrocarbons, water washing said liquid hydrocarbon and said gaseous phase to recover oxygenates therefrom, separating the liquid hydrocarbon phase and said gaseous phase under conditions to recover $C_2$ and lower boiling gaseous material, a $C_3$–$C_4$ rich hydrocarbon fraction, a gasoline boiling fraction comprising $C_5$ and higher boiling material, a light oil fraction extending in boiling range from the separated gasoline fraction up to about 600° F, and a high boiling waxy hydrocarbon fraction boiling above about 600° F, hydrodewaxing said high boiling waxy fraction in the presence of a crystalline zeolite conversion catalyst having a pore diameter greater than about 5 Angstroms; a silica-to-alumina ratio of at least 12; and a constraint index within the range of 1 to 12 which is suitable for the purpose of producing a low boiling fuel oil product fraction and a lower boiling fraction comprising gasoline boiling range material, combining the low boiling fuel oil product with said light oil fraction and subjecting the combined materials to hydrogenating conditions sufficiently severe to produce a stabilized fuel oil product, passing the separated $C_5$ plus gasoline fraction in contact with a crystalline zeolite having a pore diameter greater than about 5 Angstroms; a silica to alumina ratio of at least 12; and a constraint index within the range of 1 to 12 under conditions selected to produce a gasoline product of considerably improved octane rating and lower boiling gaseous materials which are thereafter separated from one another;

combining gaseous materials above separated from the octane improved gasoline product with the $C_3$–$C_4$ rich hydrocarbon fraction and thereafter contacting the gaseous materials thus combined with a catalyst promoting the formation of additional gasoline boiling component and liquified petroleum gas.

2. The method of claim 1 wherein dewaxing of the high boiling waxy fraction is accomplished with a ZSM5 crystalline zeolite containing catalyst.

3. The method of claim 1 wherein octane improving the $C_5$ plus gasoline fraction is accomplished with a ZSM5 crystalline zeolite containing catalyst.

4. The method of claim 1 wherein the $C_3$-$C_4$ rich hydrocarbon stream is converted to gasoline boiling components in the presence of a ZSM5 crystalline zeolite containing catalyst.

5. The method of claim 1 wherein the gasoline product obtained by hydrodewaxing the high boiling waxy fraction is combined with the octane improved gasoline product.

6. The method of claim 1 wherein the end point of the separated $C_5$ plus gasoline boiling material is selected from within the range of 320° F to about 400° F.

7. The method of claim 1 wherein the product effluent of hydrodewaxing is passed to a first high temperature separation zone to recover gasoline and lower boiling components from a higher boiling light fuel oil fraction suitable for passage to said hydrotreating operation, said gasoline and lower boiling fraction is cooled and passed to a low temperature separation zone wherein a separation is made to recover a gaseous product rich in hydrogen from an unstabilized gasoline product and a gaseous product rich in hydrogen is recycled to said hydrodewaxing operation.

* * * * *